US010960387B2

(12) United States Patent
Bao et al.

(10) Patent No.: US 10,960,387 B2
(45) Date of Patent: *Mar. 30, 2021

(54) CATALYST AND METHOD FOR DIRECT CONVERSION OF SYNGAS TO LIGHT OLEFINS

(71) Applicant: DALIAN INSTITUTE OF CHEMICAL PHYSICS, CHINESE ACADEMY OF SCIENCES, Liaoning (CN)

(72) Inventors: Xinhe Bao, Liaoning (CN); Feng Jiao, Liaoning (CN); Xiulian Pan, Liaoning (CN); Minzheng Ding, Liaoning (CN)

(73) Assignee: DALIAN INSTITUTE OF CHEMICAL PHYSICS, CHINESE ACADEMY OF SCIENCES, Liaoning (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/463,142

(22) PCT Filed: Dec. 4, 2017

(86) PCT No.: PCT/CN2017/114446
§ 371 (c)(1),
(2) Date: May 22, 2019

(87) PCT Pub. No.: WO2018/103603
PCT Pub. Date: Jun. 14, 2018

(65) Prior Publication Data
US 2019/0275505 A1 Sep. 12, 2019

(30) Foreign Application Priority Data
Dec. 5, 2016 (CN) .......................... 201611101851.0

(51) Int. Cl.
B01J 29/74 (2006.01)
B01J 29/78 (2006.01)
(Continued)

(52) U.S. Cl.
CPC .......... *B01J 29/783* (2013.01); *B01J 23/005* (2013.01); *B01J 23/06* (2013.01); *B01J 23/16* (2013.01); *B01J 23/26* (2013.01); *B01J 23/34* (2013.01); *B01J 23/54* (2013.01); *B01J 23/64* (2013.01); *B01J 23/6522* (2013.01); *B01J 29/70* (2013.01); *B01J 29/7015* (2013.01); *B01J 29/7049* (2013.01); *B01J 29/7065* (2013.01); *B01J 29/78* (2013.01); *B01J 29/82* (2013.01); *B01J 29/83* (2013.01); *B01J 29/84* (2013.01); *B01J 29/85* (2013.01); *B01J 29/87* (2013.01); *B01J 29/89* (2013.01); *B01J 35/0006* (2013.01); *B01J 37/0036* (2013.01); *B01J 37/04* (2013.01); *B01J 37/28* (2013.01); *B01J 37/30* (2013.01); *C07C 1/04* (2013.01); *C07C 1/043* (2013.01); *C07C 1/044* (2013.01); *C07C 1/0425* (2013.01); *C07C 1/0435* (2013.01); *C07C 1/0445* (2013.01); *C07C 1/0455* (2013.01); *C07C 1/10* (2013.01); *C07C 9/04* (2013.01); *C07C 11/04* (2013.01); *C07C 11/06* (2013.01); *C07C 11/08* (2013.01); *C07C 11/09* (2013.01); *B01J 2229/18* (2013.01); *B01J 2229/186* (2013.01); *Y02P 20/52* (2015.11)

(58) Field of Classification Search
CPC ........ B01J 29/70; B01J 29/78; B01J 29/7015; B01J 29/7049; B01J 29/7065; B01J 29/783; B01J 29/82; B01J 29/83; B01J 29/84; B01J 29/85; B01J 29/87; B01J 29/89; B01J 2229/186; B01J 2229/18; B01J 35/0006; B01J 37/0036; B01J 37/04; B01J 37/28; B01J 37/30; B01J 23/005; B01J 23/06; B01J 23/16; B01J 23/26; B01J 23/34; B01J 23/64; B01J 23/54; B01J 23/6522; Y02P 20/52; C07C 1/043; C07C 1/0435; C07C 1/0425; C07C 1/044; C07C 1/0445; C07C 1/0455; C07C 1/04; C07C 1/10; C07C 11/04; C07C 11/08; C07C 11/09; C07C 11/06
USPC ...... 502/60, 61, 63, 64, 66, 69, 73, 74, 214; 585/520, 527, 528, 532, 533, 530, 603, 585/606, 607
See application file for complete search history.

(56) References Cited

U.S. PATENT DOCUMENTS

2007/0244000 A1 10/2007 Molinier et al.

FOREIGN PATENT DOCUMENTS

| CN | 1083415 A | 3/1994 |
|----|-----------|--------|
| CN | 1537674 A | 10/2004 |

(Continued)

OTHER PUBLICATIONS

Jiao, Feng et al., "Selective Conversion of Syngas to Light Olefins," Catalysis, 6277 (351), Mar. 4, 2016, pp. 1065-1068.

*Primary Examiner* — Elizabeth D Wood
(74) *Attorney, Agent, or Firm* — Novick, Kim & Lee, PLLC; Allen Xue

(57) ABSTRACT

Direct conversion of syngas to light olefins is carried out in a fixed bed or a moving bed reactor with a composite catalyst A+B. The active ingredient of catalyst A is active metal oxide; and catalyst B is one or more than one of zeolite of CHA and AEI structures or metal modified CHA and/or AEI zeolite. A spacing between geometric centers of the active metal oxide of the catalyst A and the particle of the catalyst B is 5 µm-40 mm. A spacing between axes of the particles is preferably 100 µm-5 mm, and more preferably 200 µm-4 mm. A weight ratio of the active ingredients in the catalyst A and the catalyst B is within a range of 0.1-20 times, and preferably 0.3-5.

20 Claims, No Drawings

(51) Int. Cl.
*B01J 29/70* (2006.01)
*B01J 35/00* (2006.01)
*B01J 37/00* (2006.01)
*B01J 37/04* (2006.01)
*C07C 1/04* (2006.01)
*C07C 9/04* (2006.01)
*C07C 11/04* (2006.01)
*C07C 11/06* (2006.01)
*B01J 29/87* (2006.01)
*B01J 29/85* (2006.01)
*B01J 29/83* (2006.01)
*B01J 29/82* (2006.01)
*B01J 29/84* (2006.01)
*B01J 29/89* (2006.01)
*B01J 23/00* (2006.01)
*B01J 23/06* (2006.01)
*B01J 37/28* (2006.01)
*B01J 37/30* (2006.01)
*B01J 23/26* (2006.01)
*B01J 23/16* (2006.01)
*B01J 23/64* (2006.01)
*B01J 23/54* (2006.01)
*B01J 23/34* (2006.01)
*C07C 11/08* (2006.01)
*B01J 23/652* (2006.01)
*C07C 1/10* (2006.01)
*C07C 11/09* (2006.01)

(56) References Cited

FOREIGN PATENT DOCUMENTS

| | | |
|---|---|---|
| CN | 103508828 A | 1/2014 |
| WO | 2016007607 A1 | 1/2016 |

CATALYST AND METHOD FOR DIRECT CONVERSION OF SYNGAS TO LIGHT OLEFINS

TECHNICAL FIELD

The present invention relates to preparation of light olefins using syngas, and particularly relates to a catalyst and a method for preparing light olefins from direct conversion of syngas.

BACKGROUND

Light olefins refer to alkenes with the number of carbon atoms less than or equal to 4. Light olefins represented by ethylene and propylene are very important basic organic chemical raw materials. With the fast growth of economy in China, the market of the light olefins is in short supply for a long time. At present, the light olefins are produced mainly through a petrochemical route of cracking of light hydrocarbons (ethane, naphtha and light diesel fuel). Due to the increasing shortage of global petroleum resources and the long-term high price of crude oil, the development of the light olefins industry relying only on a tubular cracking furnace technology based on petroleum light hydrocarbons as raw material will encounter more and more difficulties in raw material. The technology and the raw material for producing the light olefins must be diversified. The source of the raw material can be widen by technologies based on syngas for the production of light olefins, which can be derived from crude oil, natural gas, coal and renewable materials, thus provide an alternative solution for the steam cracking technology based on the high-cost raw materials like naphtha. One-step direct preparation of the light olefins using the syngas is a process of directly preparing the light olefins with the number of carbon atoms less than or equal to 4 through Fischer-Tropsch synthesis reaction of carbon monoxide and hydrogen under the action of the catalyst. This process simplifies the process flow and greatly reduces the investment unlike an indirect method that further prepares the alkene from the syngas through the methanol or dimethyl ether.

Direct preparation of light olefins using syngas through Fischer-Tropsch synthesis has become one of research hotspots in the development of catalysts for Fischer-Tropsch synthesis. In patent CN1083415A disclosed by Dalian Institute of Chemical Physics, Chinese Academy of Sciences, high activity (CO conversion rate: 90%) and selectivity (light olefins selectivity: 66%) can be obtained under reaction pressure of 1.0 to 5.0 MPa and reaction temperature of 300 to 400° C., catalyzed by an iron-manganese catalyst system, with IIA alkali metal oxide such as MgO or silica rich zeolite (or phosphorous-aluminum zeolite) as the support, and alkali K or Cs ion as the auxiliary. In patent ZL03109585.2 declared by Beijing University of Chemical Technology, Fe/activated carbon catalyst with manganese, copper, zinc, silicon or potassium as auxiliaries is prepared by a vacuum impregnation method for the reaction of preparation of the light olefins from the syngas. Under this catalyst, the CO conversion rate is 96%, and the selectivity of light olefins in hydrocarbons is 68%, with no feedstock gas circulation. Recently, Professor de Jong's team at Utrecht University in Netherlands made good progress by using Fe catalyst modified by Fe, Na or S, and supported on SiC, carbon nanofiber or other inert carriers, obtained 61% of selectivity of light olefins. However, the selectivity of light olefins will reduce when the syngas conversion increases. In direct preparation of alkenes from syngas, cryogenic separation is generally needed due to the gaseous raw material and low-boiling ethylene product. If $C_3$-$C_4$ alkenes, i.e., propylene and butylene, can be obtained with high selectivity, cryogenic separation will not be needed, thereby greatly reducing energy consumption and cost for product separation and bringing great application value. In the above reports, metal iron or iron carbide was applied as the active component of the catalyst, and the reactions followed the carbon chain growth mechanism on metal surfaces. The selectivity of the product light olefins is low, while the selectivity of $C_3$-$C_4$ alkene is lower.

Recently, a bifunctional catalyst with the composite of $ZnCr_2O_4$ oxide and hierarchical pore SAPO-34 zeolite has been reported by Dalian Institute of Chemical Physics, Chinese Academy of Sciences (Jiao et al., Science 351 (2016) 1065-1068), which realized 80% of the selectivity of light olefins when the CO conversion was 17%. The selectivity of light paraffins was 14% so the olefin/paraffin ratio of light hydrocarbons (o/p) was 5.7. When CO conversion increased to 35%, the selectivity of light olefins was 69%, the selectivity of light paraffins was 20%, making an o/p of 3.5, and propylene and butylene selectivity was 40-50%.

SUMMARY

In view of the above problems, the present invention provides a catalyst and a method for preparing light olefins by direct conversion of syngas.

The technical solution of the present invention is as follows:

A catalyst, characterized in that, the catalyst is a composite catalyst A+B and is formed by compounding catalyst A and catalyst B in a mechanical mixing mode; the active ingredient of the catalyst A is active metal oxide; the catalyst B is a zeolite of CHA and/or AEI topology; and the active metal oxide is one or more than one of MnO, $MnCr_2O_4$, $MnAl_2O_4$, $MnZrO_4$, ZnO, $ZnCr_2O_4$, $ZnAl_2O_4$, $CoAl_2O_4$ and $FeAl_2O_4$.

A spacing between geometric centers of the active metal oxide of the catalyst A and the particle of the catalyst B is 5 μm-40 mm. A spacing between axes of the particles is preferably 100 μm-5 mm, and more preferably 200 μm-4 mm.

A weight ratio of the active ingredients in the catalyst A and the catalyst B is within a range of 0.1-20 times, and preferably 0.3-5.

The active metal oxide is composed of crystal grains with a size of 5-30 nm, and a large amount of oxygen vacancies exist within a distance range of 0.3 nm from the surfaces of the crystal grains to the internal direction of the crystal grains, i.e., the molar weight of oxygen atoms occupies a value less than 80% compared with the theoretical stoichiometric ratio; and preferably, the molar weight of oxygen atoms occupies a value of 80%-10% of the oxygen molar content in theoretical stoichiometric ratio, more preferably 60%-10% and most preferably 50%-10%. The surface oxygen vacancies are defined as: (1—the molar weight of oxygen atoms in theoretical stoichiometric ratio of oxygen molar weight); and corresponding oxygen vacancy concentration is preferably 20%-90%, more preferably 40%-90% and most preferably 50%-90%.

A dispersing agent is also added to the catalyst A; the dispersing agent is one or more than one of $Al_2O_3$, $SiO_2$, $Cr_2O_3$, $ZrO_2$ and $TiO_2$; the active metal oxide is dispersed in the dispersing agent; and the content of the dispersing agent in the catalyst A is 0.05-90 wt %, and the balance is the active metal oxide.

The catalyst component B is a zeolite of CHA and/or AEI topology. The CHA and/or AEI zeolite has eight-membered ring orifices and a three-dimensional porous channel and comprises cha cage.

The skeleton element composition of the zeolite of CHA and AEI topologies may be one or more than one of Si—O, Si—Al—O, Si—Al—P—O, Al—P—O, Ga—P—O, Ga—Si—Al—O, Zn—Al—P—O, Mg—Al—P—O and Co—Al—P—O.

H may be connected or not connected to the O element of the zeolite skeleton. The H may be entirely or partially replaced by one or more than one of Na, Ca, K, Mg, Ge, Zr, Zn, Cr, Ga. Sn, Fe, Co, Mo and Mn by ion exchange; and the total molar ratio of the substitute metal to oxygen is 0.0002-0.001.

A molar ratio of (Si+Zn+Mg+Co) to (Al+Ga) in the zeolite composition Si—O of the CHA topology and in the skeleton element composition outside is less than 0.6.

A molar ratio of (Si+Zn+Mg+Co) to (Al+Ga) in the zeolite composition Si—O of the AEI topology and in the skeleton element composition outside is less than 0.6.

The zeolite has the amount of medium-strength acidic sites of 0-0.3 mol/kg, preferably 0.003-0.2 mol/kg, and more preferably 0.003-0.06 mol/kg, wherein the peak temperature range corresponding to the desorption peak of NH3-TPD for mediate strong acid is 275-500° C., and preferably 275-370° C.

The acid strength is defined by the peak temperature of NH3-TPD, including three kinds of acid: weak acid, medium-strength acid and strong acid.

The $NH_3$-TPD is according to the position of a desorption peak of NH3; the position of the desorption peak means that under standard test conditions that a ratio of sample mass w and carrier gas flow rate f (w/f) is 100 g·h/L, and a heating rate is 10° C./min, a TCD records a thermal conductivity signal of desorption of NH3 and draws a desorption curve; according to the peak temperatures of the NH3 desoption curve, the acid strength of inorganic solid is divided into three kinds; the weak acid is an acid site where the deposition temperature of NH3 is less than 275° C.; the medium-strength acid is an acid site where the deposition temperature of NH3 is between 275° C. and 500° C.; and the strong acid is an acid site where the deposition temperature of NH3 is greater than 500° C.

The mechanical mixing can adopt one or more than one of mechanical agitation, ball milling, rocking bed mixing and mechanical grinding for composition.

A method for preparing light olefins using direct conversion of syngas, wherein syngas is used as reaction raw material; a conversion reaction is conducted on a fixed bed or a moving bed; and the catalyst used is the catalyst of any one of claims 1-8.

The pressure of the syngas is 0.5-10 MPa; reaction temperature is 300-600° C.; and space velocity is 300-10000 $h^{-1}$.

The ratio of syngas $H_2$/CO for reaction is 0.2-3.5, and preferably 0.3-2.5.

The dual-function composite catalyst is used for preparing lower alkene using one-step direct conversion of syngas, wherein the selectivity for propylene and butylene is 40-75%, and preferably 50-75%, while the selectivity for methane side product is lower than 15%, and preferably less than 10%.

The present invention has the following beneficial effects that:

Different from the traditional technology for preparing the light olefins through methanol (MTO for short), this technology realizes the preparation of light olefins through one-step direct conversion of syngas.

Propylene and butylene selectivity is as high as 40-75%. The products can be separated without deep cooling, thereby greatly reducing separation energy consumption and cost.

The composite catalyst in the patent is simple in preparation process and mild in conditions. The creaction process has an extremely high product yield and selectivity, with the selectivity for $C_2$-$C_4$ light olefins reaching 50-90% and especially high selectivity for $C_3$-$C_4$ alkenes. Meanwhile, the selectivity for methane side product is low (<15%), and the catalyst has a long lifetime greater than 700 hours. The present invention has excellent application prospect.

DETAILED DESCRIPTION

The present invention is further illustrated below by embodiments, but the scope of claims of the present invention is not limited by the embodiments. Meanwhile, the embodiments only give some conditions for achieving the purpose, but it doesn't mean that the conditions must be satisfied to achieve the purpose.

Embodiment 1

I. Preparation of Catalyst A (I) Synthesizing ZnO material with a polar surface through etching:

(1) weighing 0.446 g (1.5 mmol) of $Zn(NO_3)_2 \cdot 6H_2O$; weighing 0.480 g (12 mmol) of NaOH and adding to the above container; weighing 30 ml of deionized water and adding to the container; stirring for a time greater than 0.5 h to uniformly mix the solution; increasing the temperature to 160° C., and reaction time of 20 h; decomposing and precipitating to form zinc oxide; naturally cooling to room temperature; centrifugally separating reaction liquid to collect the centrifugally separated precipitate; and washing with deionized water twice to obtain ZnO oxide;

(2) ultrasonically mixing an etching agent with ZnO oxide uniformly under room temperature; immersing the ZnO oxide in the solution of the etching agent; and forming a complex or conducting direct reduction reaction between the etching agent and the zinc oxide; and heating the above suspension; then retrieving the suspension for washing and filtering to obtain the active nano ZnO material having a large amount of surface oxygen holes.

In Table 1: the mass ratio between the catalyst to the etching agent is 1:3. The mass ratio between the oleic acid to the hexamethylenetetramine is 1:1, without solvent. The mass ratio between the oleic acid to the hydrazine hydrate is 95:5, without solvent. Specific treatment conditions include temperature, treatment time and atmosphere types as shown in Table 1 below.

(3) Drying or Drying and Reducing:

after centrifuging or filtering the above obtained products and washing the products with deionized water, drying or drying and reducing the products in an atmosphere which is an inert atmosphere gas or a gas mixture of inert gas and a reducing gas, wherein the inert gas is one or more than one of $N_2$, He and Ar, the reducing gas is one or both of $H_2$ and CO, a volume ratio between the inert atmosphere gas to the reducing gas in the drying and reducing gas mixture is 100/10-0/100, the temperature of drying and reducing is 350° C., and time is 4 h. ZnO material with abundant oxygen vacancies on the surface is obtained. Specific samples and preparation conditions thereof are shown in Table 1 below. The oxygen vacancies on the surface are: 100%-percent of the molar weight of oxygen atoms in theoretical stoichiometric ratio of oxygen molar weight.

TABLE 1

Preparation of ZnO Material and Parameter Performance

| Sample Number | Etching Agent | Temperature/° C. and Carrier Gas (V/V) | Time/Minute | Drying or Drying and Reducing Temperature/° C. and Atmosphere | Surface Oxygen Vacancy |
|---|---|---|---|---|---|
| ZnO 1 | oleic acid-hexamethylenetetramine | 100, $N_2$ | 30 | 30, $N_2$ | 21% |
| ZnO 2 | oleic acid | 100, 5% $H_2/N_2$ | 30 | 300, 5% $H_2/N_2$ | 45% |
| ZnO 3 | oleic acid | 120, 5% CO/Ar | 60 | 350, 5% CO/Ar | 67% |
| ZnO 4 | oleic acid-5 wt % hydrazine hydrate | 140, 5% $H_2$/Ar | 60 | 310, 5% $H_2$/Ar | 73% |
| ZnO 5 | quadrol | 100, 5% $NH_3$/Ar | 30 | 250, 5% $NH_3$/Ar | 30% |
| ZnO 6 | quadrol | 140, 5% NO/Ar | 90 | 150, 5% NO/Ar | 52% |
| ZnO 7 | 20 wt % ammonium hydroxide | 100, Ar | 30 | 120, 5% CO/Ar | 22% |
| ZnO 8 | 20 wt % ammonium hydroxide | 140, 5% $NH_3$/5% NO/Ar | 90 | 400, He | 29% |

The surface oxygen vacancies are the percent of the molar weight of oxygen atoms in theoretical stoichiometric ratio of oxygen molar content within a distance range of 0.3 nm from the surfaces of the crystal grains to the internal direction of the crystal grains. The surface oxygen vacancies are defined as: 100%-percent of the molar weight of oxygen atoms in theoretical stoichiometric ratio of oxygen molar weight.

As comparative examples, ZnO 9 which has not been etched as in step (2) and has no oxygen vacancy on the surface; and metal Zn 10 has been completely reduced.

(II) Synthesizing MnO material with a polar surface by etching: the preparation process was the same as that of the above ZnO. The difference is that, the precursor of Zn has been replaced by the corresponding precursor of Mn, which is one of manganous nitrate, manganese chloride and manganese acetate (manganous nitrate herein).

The etching process is the same as step (2) in above (I), and the process of drying or drying and reducing is the same as the preparation processes of products ZnO 3, ZnO 5 and ZnO 8 in step (3) in above (I). The catalyst having a large amount of surface oxygen vacancies is synthesized. The surface oxygen vacancies are 67%, 29%, and 27%, which correspond to MnO 1, MnO 2, and MnO 3. (III) Synthesizing nano $ZnCr_2O_4$, $ZnAl_2O_4$, $MnCr_2O_4$, $MnAl_2O_4$ and $MnZrO_4$ spinel with high specific surface area and high surface energy:

selecting corresponding nitrate, zinc nitrate, aluminum nitrate, chromic nitrate or manganous nitrate as the precursor according to chemical composition of the spinel, and mixing the precursor with urea at room temperature in water; aging the above mixed liquid; then removing solids from the mixed liquid for washing, filtering and drying the obtained precipitants; and calcining the obtained solids in air to obtain spinel oxide which grows along the (110) crystal plane direction. The sample was also treated by etching to form a large amount of surface oxygen vacancies on the catalyst. The etching process and aftertreatment process are the same as step (2) and step (3) in above (I). The sample has large specific surface area and many surface defects, and can be applied to catalyzing the conversion of syngas.

Specific samples and preparation conditions thereof are shown in Table 2 below. Similarly, the surface oxygen vacancies are defined as: 100%-percent of the molar weight of oxygen atoms in theoretical stoichiometric ratio of oxygen molar weight.

TABLE 2

Preparation of Spinel Material and Performance Parameters

| Sample Number | Stoichiometric Ratio of Metal Elements in Spinel and Molar Concentration of one Metal in Water (mmol/L) | Aging Temperature ° C. and Time h | Calcining Temperature ° C. and Time h | Etching Agent, Temperature/° C., Atmosphere and Time/min | Surface Oxygen Vacancy |
|---|---|---|---|---|---|
| spinel 1 | ZnCr = 1:2, Zn is 50 mM | 120, 24 | 600, 48 | oleic acid, 120, 5% $H_2$/Ar, 60 | 41% |
| spinel 2 | ZnAl = 1:2, Zn is 50 mM | 130, 20 | 700, 24 | oleic acid, 120, 5% $H_2$/Ar, 60 | 72% |
| spinel 3 | MnCr = 1:2, Mn is 50 mM | 140, 18 | 750, 16 | oleic acid, 120, 5% $H_2$/Ar, 60 | 83% |
| spinel 4 | MnAl = 1:2, Mn is 50 mM | 145, 16 | 800, 10 | oleic acid, 120, 5% $H_2$/Ar, 60 | 20% |
| spinel 5 | MnZr = 1:2, Mn is 50 mM | 150, 12 | 900, 3 | oleic acid, 120, 5% $H_2$/Ar, 60 | 24% |

(IV) $Cr_2O_3$, $Al_2O_3$ or $ZrO_2$ dispersed active metal oxide

Preparing $Cr_2O_3$, $Al_2O_3$ or $ZrO_2$ dispersed active metal oxide through precipitation using $Cr_2O_3$, $Al_2O_3$ or $ZrO_2$ as the carrier. Taking the preparation of dispersed ZnO as an example, commercial $Cr_2O_3$, $Al_2O_3$ or $ZrO_2$ carrier was dispersed in a base solution in advance, and then one or more than one of zinc acetate, zinc nitrate, zinc sulfate and other Zn precursors were used as Zn raw material, mixed with one or more than one of sodium hydroxide, ammonium bicarbonate, ammonium carbonate and sodium bicarbonate, and precipitated at room temperature. Herein, taking zinc nitrate and sodium hydroxide as an example, the molar concentration of $Zn^{2+}$ in the reaction liquid is 0.067M; the ratio of molar fractions of $Zn^{2+}$ and precipitant may be 1:8; and then aging is conducted at 160° C. for 24 hours to obtain carrier $Cr_2O_3$, $Al_2O_3$ or $ZrO_2$ dispersed ZnO oxide, and the contents of the dispersing agents in catalyst A are 0.1 wt %, 10 wt % and 90 wt %.

The etching process is the same as the preparation processes of products ZnO 3, ZnO 5 and ZnO 8 in step (2) in above (I). The catalyst having a great number of surface oxygen vacancies was obtained. The aftertreatment process is the same as step (3) in above (I). The surface oxygen vacancies are 65%, 30% and 25%, which corresponds to dispersed oxide 1, dispersed oxide 2, and dispersed oxide 3, respectively.

The same method is used to obtain MnO oxides dispersed in carrier $Cr_2O_3$, $Al_2O_3$ or $ZrO_2$, wherein the contents of the dispersing agents in catalyst A are 5 wt %, 30 wt % and 60 wt %. The surface oxygen vacancies are 62%, 27% and 28%, which corresponds to dispersed oxide 4, dispersed oxide 5, and dispersed oxide 6.

II. Preparation of Catalyst B (Zeolite of CHA and AEI Topologies):

The CHA and/or AEI topology has eight-membered ring orifices, a three-dimensional porous channel, and CHA cages.

1) The specific preparation process is as follows:

The raw materials include silica sol (30% mass concentration), AlOOH, phosphoric acid, TEA (R) and deionized water were weighed according to the mass ratio of oxides $SiO_2:Al_2O_3:H_3PO_4:R:H_2O=1.6:16:32:55:150$; after mixing at room temperature, auxiliary HF was added with a molar weight of 0.5 time of the template agent; the mixture was stirred and aged at 30° C. for 2 h, and transferred into a hydrothermal reactor and crystallized at 200° C. for 24 h. The autoclave was quenched by water bath to room temperature. Centrifugal washing was conducted repeatedly until the pH of the supernatant reached 7 at the end of washing. After the precipitate had been dried at 110° C. for 17 h, the precipitate was calcined in air at 600° C. for 3 h to obtain the silicon-phosphorus-aluminum inorganic solid acid with a hierarchical pore structure.

The skeleton element composition of the zeolite of CHA and AEI topologies may be one or more than one of Si—O, Si—Al—O, Si—Al—P—O, Al—P—O, Ga—P—O, Ga—Si—Al—O, Zn—Al—P—O, Mg—Al—P—O and Co—Al—P—O. Some of oxygen atoms on the skeleton are connected with H, and corresponding products are successively defined as zeolites 1-8.

TABLE 3

Preparation of Zeolite of CHA or AEI Topology and Performance Parameters

| Sample Number | Si Source | Aluminum Source | P Source | Template Agent | Auxiliary | Mass Ratio | Hydrothermal Temperature (° C.) | Time (Day) | Acid Amount | Deposition Temperature of $NH_3$ |
|---|---|---|---|---|---|---|---|---|---|---|
| Zeolite 1 | TEOS | Sodium Meta-aluminate | Phosphoric Acid | TEA | | $SiO_2:Al_2O_3:H_3PO_4:R:H_2O$ = 1.6:16:32:55:150 | 180 | 1 | 0.25 | 349 |
| Zeolite 2 | Silica Sol | Al(OH)$_3$ | Phosphoric Acid | Mor | HCl | $SiO_2:Al_2O_3:H_3PO_4:R:H_2O$ = 2.4:19:30:15:150 | 150 | 4 | 0.27 | 365 |
| Zeolite 3 | TEOS | AlOOH | Phosphoric Acid | TEAOH | HF | $SiO_2:Al_2O_3:H_3PO_4:R:H_2O$ = 0.7:15:32:55:150 | 160 | 4 | 0.13 | 350 |
| Zeolite 4 | Silica Sol | Aluminium Isopropoxide | Phosphoric Acid | DIPEA | | $SiO_2:Al_2O_3:H_3PO_4:R:H_2O$ = 1.1:17:32:55:150 | 170 | 2.5 | 0.23 | 355 |
| Zeolite 5 | | Aluminum Sulfate | Phosphoric Acid | TEAOH | HF | $Al_2O_3:H_3PO_4:R:H_2O$ = 16:32:55:150 | 190 | 1 | 0.006 | 331 |
| Zeolite 6 | Silica Sol | Aluminum Nitrate | Phosphoric Acid | DIPEA | | $SiO_2:Al_2O_3:H_3PO_4:R:H_2O$ = 0.5:17:32:55:150 | 200 | 1 | 0.078 | 344 |
| Zeolite 7 | TEOS | Aluminum Sulfate | Phosphoric Acid | TEA | HF | $SiO_2:Al_2O_3:H_3PO_4:R:H_2O$ = 0.3:18:32:55:150 | 170 | 0.7 | 0.055 | 347 |
| Zeolite 8 | | Aluminum Nitrate | Phosphoric Acid | TEA | HCl | $Al_2O_3:H_3PO_4:R:H_2O$ = 11:32:55:150 | 160 | 3.5 | 0.014 | 339 |

2) Hydrogen atoms connected to oxygen atoms in skeletons of the above products 1-7 were partly replaced by the following metal ions: Na, Ca, K, Mg, Ge, Zr, Zn, Cr, Ga. Sn, Fe, Co, Mo and Mn by ion exchange; and the preparation process is:

$SiO_2:Al_2O_3:H_3PO_4:R:H_2O=1.1:16:32:55:150$ (molar ratio), wherein R is the template agent.

The aluminum sulphate was mixed with the sodium hydroxide solution, and then silica sol, phosphoric acid, TEA(R) and deionized water were added and stirred for 1 h to obtain initial gel with uniform phase. Then, the mixture was transferred into a synthesis autoclave, was statically crystallized at 165° C. for 80 h, and then quenched, washed and dried to obtain zeolite samples.

The above samples were then mixed with 0.5 mol/L of metal ion nitrate solution to be exchanged with the solid-liquid mass ratio of 1:30. The mixture was stirred at 80° C. for 6 h, washed and dried. The exchange procedure was conducted twice continuously, and the as-prepared powder was calcined at 550° C. for 3 h to obtain CHA or AEI zeolite after metal ion exchange.

Corresponding products are successively designated as zeolites 9-22.

TABLE 4

Preparation of Zeolite of CHA or AEI Topology and Performance Parameters

| Sample Number | Ion | Ratio of metal ion and O | $NH_3$-zeolites | Aluminum Source | Exchange Temperature (° C.) | Time (hour) | Acid Amount | Deposition Temperature of $NH_3$ |
|---|---|---|---|---|---|---|---|---|
| zeolite 9 | Na | 0.04 | Zeolite 1 | Sodium Metaaluminate | 80 | 8 | 0.23 | 367 |
| Zeolite 10 | Ca | 0.02 | Zeolite 2 | Al(OH)$_3$ | 90 | 7 | 0.03 | 364 |
| Zeolite 11 | K | 0.01 | Zeolite 3 | AlOOH | 80 | 7 | 0.11 | 357 |
| Zeolite 12 | Mg | 0.015 | Zeolite 4 | Aluminium Isopropoxide | 90 | 5 | 0.08 | 355 |
| Zeolite 13 | Ge | 0.075 | Zeolite 5 | Aluminum Sulfate | 80 | 7 | 0.15 | 367 |
| Zeolite 14 | Zr | 0.03 | Zeolite 6 | Aluminum Sulfate | 90 | 7 | 0.05 | 347 |
| Zeolite 15 | Zn | 0.005 | Zeolite 7 | Aluminum Sulfate | 80 | 8 | 0.10 | 370 |
| Zeolite 16 | Cr | 0.07 | Zeolite 8 | Aluminum Nitrate | 70 | 3 | 0.25 | 363 |
| Zeolite 17 | Ga | 0.01 | Zeolite 1 | Aluminum Nitrate | 80 | 6 | 0.17 | 354 |
| Zeolite 18 | Sn | 0.001 | Zeolite 2 | AlOOH | 60 | 5 | 0.27 | 357 |
| Zeolite 19 | Fe | 0.0005 | Zeolite 3 | Aluminum Nitrate | 70 | 5 | 0.23 | 366 |
| Zeolite 20 | Co | 0.0003 | Zeolite 4 | Aluminum Nitrate | 80 | 6 | 0.18 | 367 |
| Zeolite 21 | Mo | 0.0005 | Zeolite 5 | Aluminum Nitrate | 70 | 3 | 0.28 | 369 |
| Zeolite 22 | Mn | 0.002 | Zeolite 6 | AlOOH | 70 | 8 | 0.29 | 359 |

TABLE 5

Preparation of Zeolite Composed of Other Elements and Performance Parameters

| Sample Number | Precursor 1 | Precursor 2 | Precursor 3 | Template Agent | Auxiliary | Mass Ratio |
|---|---|---|---|---|---|---|
| Zeolite 23 | TEOS | | | TEA | HF | SiO$_2$:R:H$_2$O = 1.6:55:150 |
| Zeolite 24 | Silica Sol | Al(OH)$_3$ | | Mor | HF | SiO$_2$:Al$_2$O$_3$:R:H$_2$O = 2.4:19:15:150 |
| Zeolite 25 | | Gallium Nitrate | Phosphoric Acid | TEAOH | HF | Ga2O3:H$_3$PO$_4$:R:H$_2$O = 15:32:55:150 |
| Zeolite 26 | Silica Sol | Gallium Nitrate | Phosphoric Acid | TEA | HF | SiO$_2$:Ga$_2$O$_3$:H$_3$PO$_4$:R:H$_2$O = 1.1:17:32:55:150 |
| Zeolite 27 | Zinc Nitrate | Aluminum Sulfate | Phosphoric Acid | TEAOH | HF | ZnO:Al$_2$O$_3$:H$_3$PO$_4$:R:H$_2$O = 0.5:16:32:55:150 |
| Zeolite 28 | Magnesium Nitrate | Aluminum Nitrate | Phosphoric Acid | TEA | | MgO:Al$_2$O$_3$:H$_3$PO$_4$:R:H$_2$O = 0.5:17:32:55:150 |
| Zeolite 29 | Cobalt Nitrate | Aluminum Sulfate | Phosphoric Acid | TEA | HF | SiO$_2$:Al$_2$O$_3$:H$_3$PO$_4$:R:H$_2$O = 0.4:18:32:55:150 |

| Sample Number | Hydrothermal Temperature (° C.) | Time (Day) | Acid Amount | Temperature of Desorption Peak Point of Mediate Strong Acid on NH$_3$-TPD (° C.) |
|---|---|---|---|---|
| Zeolite 23 | 180 | 1 | 0.004 | 344 |
| Zeolite 24 | 150 | 4 | 0.11 | 357 |
| Zeolite 25 | 160 | 4 | 0.012 | 347 |
| Zeolite 26 | 170 | 2.5 | 0.07 | 343 |
| Zeolite 27 | 190 | 1 | 0.0506 | 360 |
| Zeolite 28 | 200 | 1 | 0.178 | 357 |
| Zeolite 29 | 170 | 0.7 | 0.255 | 363 |

III. Catalyst Preparation

The catalyst A and the catalyst B in the required ratio are added to the container to achieve the purposes of separation, crushing, or uniform mixing, etc., through one or more than one of extrusion force, impact force, shear force and friction force generated by high-speed motion of the material and/or the container, and realize conversion among mechanical energy, thermal energy and chemical energy by regulating the temperature and the type of carrier gas, thereby further enhancing the interaction between different components.

In the mechanical mixing process, the mixing temperature can be set as 20-100° C., and the mechanical mixing process can be conducted in an atmosphere or directly in the air. The atmosphere was one or more of: a) nitrogen and/or inert gas; b) mixed gas of hydrogen, nitrogen and/or inert gas, with the volume ratio of hydrogen in the mixed gas being 5-50%; c) mixed gas of carbon monoxide, nitrogen and/or inert gas, with the volume ratio of carbon monoxide in the mixed gas being 5-20%; and d) mixed gas of oxygen, nitrogen and/or inert gas, with the volume ratio of oxygen in the mixed gas being 5-20%. The inert gas was one or more of helium, argon and neon.

Mechanical stirring: mixing the catalyst A and the catalyst B with a stirring rod in a stirring tank; and regulating the mixing degree and the relative distance of the catalyst A and the catalyst B by controlling stirring time (5 min-120 min) and rate (30-300 r/min).

Ball milling: Rolling the abrasive and the catalysts at a high speed in a grinding tank thus producing strong impact and milling on the catalysts to achieve the effects of dispersing and mixing the catalyst A and the catalyst B. The ratio of the abrasive (which is stainless steel, agate and quartz; and the size range is 5 mm-15 mm) to the catalysts (the mass ratio scope is 20-100:1) is controlled to regulate the particle size and the relative distance of the catalysts.

Shaking table mixing: premixing the catalyst A and the catalyst B and placing the catalysts into the container; realizing the mixing of the catalyst A and the catalyst B by controlling the reciprocating oscillation or circumferential oscillation of the shaking table; and realizing uniform mixing and regulating the relative distance by regulating oscillation speed (range: 1-70 r/min) and time (range: 5 min-120 min).

Mechanical grinding: premixing the catalyst A and the catalyst B and placing the catalysts into a container; and under a certain pressure (range: 5 kgf/cm$^2$-20 kgf/cm$^2$), making the ground and the mixed catalysts do relative motions (speed range: 30-300 r/min) to achieve the effects of regulating the particle size and the relative distance of the catalysts and realizing uniform mixing.

Specific catalyst preparation and parameter features are shown in Table 6.

TABLE 6

Preparation of Catalysts and Parameter Features

| Catalyst Number | Catalyst Component A | Catalyst Component B | Weight Ratio of A to B | Mechanical Stirring Rate (r/min) and Time (min) | Ball Milling Abrasive Material, Size Range and Catalyst Mass Ratio | Shaking Table Oscillation Speed (r/min) and Time (min) | Mechanical Grinding Pressure (kg) and Relative Motion Rate (r/min) | Geometrical Center Distance of A and B Particles |
|---|---|---|---|---|---|---|---|---|
| A | ZnO1 | Zeolite 1 | 0.33 | 5, 30 | | | | 3 mm |
| B | ZnO 2 | Zeolite 2 | 0.5 | 100, 250 | | | | 500 μm |
| C | ZnO3 | Zeolite 3 | 2 | | 5 mm stainless steel ball, 50:1 | | | 52 μm |
| D | ZnO4 | Zeolite 4 | 1 | | 6 mm stainless steel ball, 60:1 | | | 8 μm |
| E | ZnO 5 | Zeolite 5 | 1 | | | 5, 10 | | 2 mm |
| F | ZnO 6 | Zeolite 6 | 3 | | | 60, 100 | | 600 μm |
| G | ZnO 7 | Zeolite 7 | 3 | | | | 5, 30 | 300 μm |
| H | ZnO 8 | Zeolite 8 | 1 | 100, 300 | | | | 400 μm |
| I | spinel 1 | Zeolite 9 | 5 | | 6 mm agate ball, 100:1 | | | 30 μm |
| | spinel 2 | Zeolite 10 | 1 | | | 70, 100 | | 500 μm |
| K | spinel 3 | Zeolite 11 | 3 | | | | 15, 200 | 150 μm |
| L | spinel 4 | Zeolite 12 | 0.33 | | | | 20, 300 | 100 μm |
| M | spinel 5 | Zeolite 13 | 1 | 100, 300 | | | | 400 μm |
| N | MnO 1 | Zeolite 14 | 3 | | 6 mm quartz, 100:1 | | | 15 μm |
| O | MnO 2 | Zeolite 15 | 0.33 | | 6 mm quartz, 100:1 | | | 15 μm |
| P | MnO 3 | Zeolite 16 | 1 | | | | 10, 100 | 100 μm |
| Q | dispersed oxide 1 | Zeolite 17 | 1 | 100, 250 | | | | 2 mm |
| R | dispersed oxide 2 | Zeolite 18 | 3 | | 5 mm stainless steel ball, 50:1 | | | 50 μm |

TABLE 6-continued

Preparation of Catalysts and Parameter Features

| Catalyst Number | Catalyst Component A | Catalyst Component B | Weight Ratio of A to B | Mechanical Stirring Rate (r/min) and Time (min) | Ball Milling Abrasive Material, Size Range and Catalyst Mass Ratio | Shaking Table Oscillation Speed (r/min) and Time (min) | Mechanical Grinding Pressure (kg) and Relative Motion Rate (r/min) | Geometrical Center Distance of A and B Particles |
|---|---|---|---|---|---|---|---|---|
| S | dispersed oxide 3 | Zeolite 19 | 1 | | | | 10, 100 | 100 μm |
| T | dispersed oxide 4 | Zeolite 20 | 4 | | | 50, 60 | | 1 mm |
| U | dispersed oxide 5 | Zeolite 21 | 3 | | | | 10, 100 | 100 μm |
| V | dispersed oxide 6 | Zeolite 22 | 20 | | 5 mm stainless steel ball, 100:1 | | | 5 μm |
| W | ZnO1 | Zeolite 23 | 0.5 | 5, 30 | | | | 3 mm |
| X | ZnO 2 | Zeolite 24 | 1 | 100, 250 | | | | 500 μm |
| Y | ZnO3 | Zeolite 25 | 3 | | 5 mm stainless steel ball, 50:1 | | | 52 μm |
| Z | ZnO4 | Zeolite 26 | 1.5 | | 6 mm stainless steel ball, 60:1 | | | 8 μm |
| Z1 | ZnO 5 | Zeolite 27 | 2.5 | | | 5, 10 | | 2 mm |
| Z2 | ZnO 6 | Zeolite 28 | 1.5 | | | 60, 100 | | 600 μm |
| Z3 | ZnO7 | Zeolite 29 | 2 | | | | 5, 30 | 300 μm |
| Z4 | MnO 1 | Zeolite 1 | 16 | 100, 200 | | | | 400 μm |
| Z5 | ZnO 1 | Zeolite 1 | 0.1 | | | | 20, 100 | 500 μm |
| Z6 | dispersed oxide 1 | Zeolite 1 | 1 | | | | 20, 300 | 100 μm |
| Z7 | spinel 1 | Zeolite 1 | 1.5 | 60, 100 | | | | 2 mm |
| Z8 | ZnO1 | Zeolite 9 | 4 | | 5 mm stainless steel ball, 50:1 | | | 15 μm |
| Z9 | MnO 1 | Zeolite 2 | 4.5 | | | 50, 120 | | 500 μm |
| Z10 | dispersed oxide 1 | Zeolite 3 | 2.5 | | | | 10, 200 | 200 μm |
| Z11 | spinel 1 | Zeolite 4 | 3 | | | | 20, 200 | 150 μm |
| Comparison 1 | ZnO 9 | Zeolite 1 | 3 | | | 20, 30 | | 2 mm |
| Comparison 2 | Zn 10 | Zeolite 1 | 2 | 60, 100 | | | | 2 mm |

Example of Catalytic Reactions

A fixed bed reaction is taken as an example, but the catalyst is also applicable to a fluidized bed reactor. The apparatus is equipped with gas mass flow meters and online product analysis chromatography (the tail gas of the reactor is directly connected with the metering valve of chromatography, and thus periodic and real-time sampling and analysis will be achieved).

2 g of the above catalyst in the present invention was placed in a fixed bed reactor. The air in the reactor was replaced with Ar; and then the temperature was raised to 300° C. in the $H_2$ atmosphere, and then the inlet gas was switched to the syngas ($H_2$/CO molar ratio=0.2-3.5). The pressure of the syngas was 0.5-10 MPa. The temperature was raised to reaction temperature of 300-600° C., and the space velocity of the reaction raw gas was regulated to 500-8000 ml/g/h. On-line chromatography is used to detect and analyze the product.

The reaction performance can be changed by changing the temperature, pressure, space velocity and $H_2$/CO molar ratio in the syngas. The sum selectivity of propylene and butylene was 30-75%. The selectivity of light olefins (the sum of ethylene, propylene and butylene) was 50-90%. Due to the low hydrogenation activity of the surface of the metal composite of the catalyst, a large amount of methane will be avoided and the selectivity of methane is low. Table 7 lists specific application and effect data of the catalysts.

TABLE 7

Specific Application and Effect Data of Catalysts

| Embodiment | Catalyst | GHSV ($h^{-1}$) | Temperature (° C.) | $H_2$/CO Molar Ratio | Pressure (MPa) | CO Conversion % | Light olefins Selectivity % | $CH_4$ Selectivity % | Propylene and Butylene Selectivity % |
|---|---|---|---|---|---|---|---|---|---|
| 1 | A | 2500 | 410 | 2 | 3.5 | 13.5 | 71.8 | 13.2 | 47.1 |
| 2 | B | 3000 | 400 | 3.5 | 0.9 | 27.3 | 65.5 | 5.3 | 43.5 |

TABLE 7-continued

Specific Application and Effect Data of Catalysts

| Embodiment | Catalyst | GHSV (h$^{-1}$) | Temperature (° C.) | H$_2$/CO Molar Ratio | Pressure (MPa) | CO Conversion % | Light olefins Selectivity % | CH$_4$ Selectivity % | Propylene and Butylene Selectivity % |
|---|---|---|---|---|---|---|---|---|---|
| 3 | C | 3000 | 360 | 3 | 2.5 | 42.5 | 70.5 | 14.2 | 55.3 |
| 4 | D | 8000 | 370 | 2 | 10 | 38.6 | 69.6 | 14.9 | 45.1 |
| 5 | E | 1000 | 470 | 3.5 | 1.5 | 20.1 | 85.8 | 13.5 | 71.3 |
| 6 | F | 2000 | 400 | 3.5 | 7 | 33.3 | 78.8 | 6.6 | 54.3 |
| 7 | G | 3000 | 380 | 1.5 | 2.5 | 10.3 | 81.2 | 11.7 | 68.6 |
| 8 | H | 500 | 370 | 2.5 | 5 | 18.6 | 78.4 | 9.8 | 64.3 |
| 9 | I | 2300 | 370 | 1 | 3.5 | 22.3 | 61.4 | 14.2 | 42.6 |
| 10 | J | 2000 | 410 | 2.5 | 8 | 33.3 | 84.7 | 11.5 | 71.9 |
| 11 | K | 1000 | 430 | 2.5 | 3 | 45.7 | 75.2 | 9.1 | 56.3 |
| 12 | L | 2500 | 520 | 1 | 4 | 15.2 | 77.2 | 14.5 | 57.7 |
| 13 | M | 3000 | 480 | 0.5 | 9 | 11.5 | 79.5 | 13.2 | 55.1 |
| 14 | N | 3100 | 470 | 3 | 6 | 40.2 | 55.5 | 12.1 | 44.5 |
| 15 | O | 3200 | 450 | 1.5 | 5 | 14.3 | 60.9 | 13.2 | 46.3 |
| 16 | P | 3000 | 450 | 2.5 | 5 | 13.8 | 75.6 | 8.9 | 41.4 |
| 17 | Q | 3000 | 350 | 3.5 | 5 | 37 | 72.2 | 8.6 | 44.3 |
| 18 | R | 2100 | 350 | 2 | 7 | 18.6 | 59.8 | 10.4 | 40.2 |
| 19 | S | 2500 | 400 | 1 | 6 | 19.6 | 70.8 | 10.7 | 45.7 |
| 20 | T | 4000 | 400 | 2 | 4 | 30.3 | 76.1 | 9.4 | 51.0 |
| 21 | U | 3500 | 400 | 3 | 3 | 16.4 | 67.8 | 11.2 | 43.4 |
| 22 | V | 3000 | 450 | 2.5 | 4 | 21.2 | 70.4 | 12.3 | 44.8 |
| 23 | W | 2500 | 410 | 2 | 3.5 | 11.3 | 85.3 | 8.9 | 71.7 |
| 24 | X | 3000 | 400 | 3.5 | 0.9 | 15.7 | 75.3 | 7.7 | 60.9 |
| 25 | Y | 3000 | 360 | 3 | 2.5 | 25.7 | 60.7 | 11.7 | 49.3 |
| 26 | Z | 8000 | 370 | 2 | 10 | 38.7 | 76.8 | 9.7 | 61.2 |
| 27 | Z 1 | 1000 | 470 | 1.5 | 1.5 | 12.5 | 85.1 | 10.8 | 72.8 |
| 28 | Z 2 | 2000 | 400 | 3.5 | 7 | 26.9 | 73.3 | 12.3 | 60.7 |
| 29 | Z 3 | 3000 | 380 | 1.5 | 2.5 | 11.3 | 65.7 | 14.9 | 49.1 |
| 30 | Z 4 | 2000 | 400 | 3 | 3.5 | 30.2 | 74.3 | 8.4 | 40.9 |
| 31 | Z5 | 2500 | 400 | 0.3 | 10 | 16.8 | 70.1 | 5.3 | 40.0 |
| 32 | Z6 | 3000 | 350 | 3 | 4 | 35.6 | 75.0 | 10.3 | 41.2 |
| 33 | Z7 | 4500 | 400 | 2.5 | 3 | 21.8 | 65.3 | 12.2 | 43.2 |
| 34 | Z8 | 4000 | 400 | 3 | 4 | 28.5 | 55.8 | 13.0 | 42.3 |
| 35 | Z9 | 2000 | 350 | 2.5 | 3 | 38.9 | 62.3 | 8.7 | 48.7 |
| 36 | Z10 | 4000 | 350 | 3 | 4 | 37.1 | 77.1 | 13.2 | 60.5 |
| 37 | Z11 | 4200 | 400 | 2.5 | 4 | 25.8 | 73.3 | 10.0 | 40.7 |
| 38 | Reference Example 1 | 3000 | 320 | 0.5 | 1 | 1.9 | 31.0 | 31.0 | 29.2 |
| 39 | Reference Example 2 | 2000 | 350 | 1 | 2 | 22.7 | 39.2 | 46.8 | 27.1 |
| 40 | Reference Example 3 | 4000 | 450 | 3 | 3 | 30.5 | 26.8 | 22.6 | 12.9 |
| 41 | Reference Example 4 | 2000 | 350 | 2.5 | 3 | 0.3 | 25.5 | 65.1 | 19.4 |
| 42 | Reference Example 5 | 2000 | 410 | 1.5 | 3 | 24.6 | 46.2 | 9.7 | 25.6 |
| 43 | Reference Example 6 | 3000 | 400 | 2 | 3.5 | 31.2 | 19.5 | 10.8 | 12.7 |
| 44 | Reference Example 7 | 3000 | 450 | 2.5 | 4 | 8.6 | 43.6 | 37.9 | 28.8 |
| 45 | Reference Example 8 | 3200 | 350 | 3 | 2.7 | 52.1 | 43.7 | 28.1 | 26.4 |

In the comparative example 1, the catalyst component A is ZnO 9, and component B is Zeolite In the comparative example 2, the catalyst component A is Zn 10, and component B is Zeolite 1.

The component A in the catalyst used in the comparative example 3 is metal ZnCo+ Zeolite 1. The molar ratio of Zn to Co is 1:1. The mass ratio of ZnCo to Zeolite 1 is 1:1. Other parameters and the mixing process are the same as those of catalyst A.

The catalyst used in the comparative example 4 is TiO$_2$ without surface oxygen vacancy+Zeolite 1. Other parameters and the mixing process are the same as those of catalyst A.

The zeolite in the catalyst used in the comparative example 5 is a commercially available SAPO-34 purchased from Nankai University Catalyst Factory, wherein the temperature of desorption peak of medium-strength acid on NH3-TPD is 390° C.

The zeolite in the catalyst used in the comparative example 6 is a commercially ZSM-5 purchased from Nankai University Catalyst Factory, wherein the zeolite is of a full microporous structure and the Si/Al ratio is 30.

Reaction results of the comparative examples 5 and 6 show that, the topological structure and acid strength of CHA or AEI are crucial to the modulation of the selectivity of products.

The distance between the metal oxide and the zeolite in the catalyst used in the comparative example 7 is 10 mm. Other parameters and the mixing process are the same as those of catalyst A.

The metal oxide in the catalyst used in the comparative example 8 is located in porous channels of the zeolite and is in close contact with the zeolite. Other parameters and the like are the same as those of catalyst A.

Results of the comparative examples 7 and 8 show that, the distance between component A and component B is also very important to product selectivity.

In the reference technology of the document (Jiao et al., Science 351 (2016) 1065-1068), the acid amount of the SAPO-34 zeolite used was large. The amount of the medium-strength acid reached 0.32 mol/kg according to the NH3-TPD test. Therefore, when the conversion increased to 35%, the selectivity of light olefins was 69%, the selectivity of light paraffins was 20%, o/p decreased to 3.5 and the selectivity of propylene and butylene was 40-50%.

It is observed from the above table that, the structure of the zeolite including the topologies, acid strength and acid amount of CHA&AEI, and the matching of the distance between the metal oxide and the zeolite are crucial and directly affect the conversion of carbon monoxide and the selectivity of propylene and butylene.

We claim:

1. A catalyst, comprising a metal oxide chosen from MnO, $MnCr_2O_4$, $MnAl_2O_4$, $MnZrO_4$, ZnO, $ZnAl_2O_4$, $CoAl_2O_4$, $FeAl_2O_4$, or mixtures thereof, and a zeolite of CHA and/or AEI topology.

2. The catalyst of claim 1, wherein the zeolite has a skeleton comprising species chosen from Si—O, Si—Al—O, Si—Al—P—O, Al—P—O, Ga—P—O, Ga—Si—Al—O, Zn—Al—P—O, Mg—Al—P—O, or Co—Al—P—O.

3. The catalyst according to claim 1, wherein the zeolite has an amount of medium-strength acid sites of 0-0.3 mol/kg, wherein the medium-strength acid sites are characterized by a peak temperature range corresponding to a desorption peak of NH3-TPD of 275-500° C., and a chemical shift of $^{13}$C-NMR in a range of 210-220 ppm using acetone as a probe molecule.

4. The catalyst according to claim 1, wherein the metal oxide and the zeolite are particles, wherein when a particle of the metal oxide and a particle of the zeolite are adjacent to each other, a spacing between a geometric center of the metal oxide particle and a geometric center of the adjacent zeolite particle is in a range of 5 μm-40 mm.

5. The catalyst according to claim 1, wherein a weight ratio between the metal oxide and the zeolite is in a range of 0.1-20.

6. The catalyst according to claim 1, wherein the metal oxide is composed of crystal grains with a size of 5-30 nm, and wherein each crystal grain has oxygen vacancies within a distance of 0.3 nm from a surface thereof to at a molar concentration of 20%-80%, wherein the molar concentration is a percentage of a mole number the oxygen vacancies and a mole number of a theoretical amount of oxygen atoms.

7. The catalyst according to claim 1, further comprising a dispersing agent chosen from $Al_2O_3$, $SiO_2$, $Cr_2O_3$, $ZrO_2$, $TiO_2$ or mixtures thereof, wherein the metal oxide is dispersed in the dispersing agent and a weight percentage of the dispersing agent in the metal oxide is 0.05-90 wt %.

8. The catalyst according to claim 1, wherein, on the skeleton of the zeolite, at least a portion of H in hydroxyl groups are substituted by one or more metal chosen from Na, Ca, K, Mg, Ge, Zr, Zn, Cr, Ga, Sn, Fe, Co, Mo, or Mn by ion exchange, and a total molar ratio of the substitute metal to oxygen is 0.0002-0.001.

9. A method for preparing light olefins using direct conversion of syngas, comprising contacting syngas with the catalyst of claim 1, wherein a pressure of syngas is 0.5-10 MPa, a reaction temperature is 300-600° C., a space velocity is 300-10000 h$^{-1}$, and a molar ratio between $H_2$ and CO in the syngas 0.2-3.5.

10. The catalyst according to claim 2, wherein the zeolite has medium-strength acid sites of 0.003-0.2 mol/kg, wherein the medium-strength acid sites are characterized by a peak temperature range corresponding to a desorption peak of NH3-TPD for medium-strength acid of 275-500° C., and a chemical shift of $^{13}$C-NMR in a range of 210-220 ppm using acetone as a probe molecule.

11. The catalyst according to claim 5, wherein, on the skeleton of the zeolite, at least a portion of H in hydroxyl groups are substituted by one or more metal chosen from Na, Ca, K, Mg, Ge, Zr, Zn, Cr, Ga, Sn, Fe, Co, Mo, Mn, or mixtures thereof by ion exchange, and a total molar ratio of the substitute metal to oxygen is 0.0002-0.001.

12. The catalyst of claim 2, wherein a molar ratio of Si:Al, Si:(Ga+Al), Zn:Al, Mg:Al, or Co:Al in the skeleton of component B is 0.001 to 0.6.

13. The catalyst of claim 2, wherein the molar ratio of Si:Al, Si:(Ga+Al), Zn:Al, Mg:Al, or Co:Al in the skeleton of component B is 0.001 to 0.48.

14. A catalyst comprising $ZnCr_2O_4$ and a zeolite of AEI topology.

15. The catalyst of claim 14, wherein the zeolite has a skeleton comprising species chosen from Si—O, Si—Al—O, Si—Al—P—O, Al—P—O, Ga—P—O, Ga—Si—Al–O, Zn—Al—P—O, Mg—Al—P—O, or Co—Al—P—O.

16. The catalyst according to claim 14, wherein $ZnCr_2O_4$ and the zeolite are particles, wherein when a particle of $ZnCr_2O_4$ and a particle of the zeolite are adjacent to each other, a spacing between a geometric center of the $ZnCr_2O_4$ particle and a geometric center of the adjacent zeolite particle is in a range of 5 μm-40 mm.

17. The catalyst according to claim 14, wherein a weight ratio between $ZnCr_2O_4$ and the zeolite is in a range of 0.1-20.

18. A method for preparing light olefins using direct conversion of syngas, comprising contacting syngas with the catalyst of claim 14, wherein a pressure of syngas is 0.5-10 MPa, a reaction temperature is 300-600° C., a space velocity is 300-10000 h$^{-1}$, and a molar ratio between $H_2$ and CO in the syngas 0.2-3.5.

19. A catalyst comprising $ZnCr_2O_4$ and a zeolite of CHA topology, wherein the zeolite has a skeleton comprising species chosen from Si—O, Si—Al—O, Si—Al—P—O, Al—P—O, Ga—P—O, Ga—Si—Al—O, Zn—Al—P—O, Mg—Al—P—O, or Co—Al—P—O, wherein the zeolite has an amount of medium-strength acid sites of 0-0.3 mol/kg, wherein the medium-strength acid sites are characterized by a peak temperature range corresponding to a desorption peak of $NH_3$-TPD of 275-500° C. and a chemical shift of $^{13}$C-NMR in a range of 210-220 ppm using acetone as a probe molecule.

20. The catalyst according to claim 19, wherein $ZnCr_2O_4$ and the zeolite are particles, wherein when a particle of $ZnCr_2O_4$ and a particle of the zeolite are adjacent to each other, a spacing between a geometric center of the $ZnCr_2O_4$ particle and a geometric center of the adjacent zeolite particle is in a range of 5 μm-40 mm.

* * * * *